(12) United States Patent
Castaneda

(10) Patent No.: US 11,833,072 B2
(45) Date of Patent: Dec. 5, 2023

(54) ERECTILE DYSFUNCTION TREATMENT SYSTEM AND METHOD

(71) Applicant: Sergio Castaneda, Las Vegas, NV (US)

(72) Inventor: Sergio Castaneda, Las Vegas, NV (US)

(*) Notice: Subject to any disclaimer, the term of this patent is extended or adjusted under 35 U.S.C. 154(b) by 92 days.

(21) Appl. No.: 17/381,167

(22) Filed: Jul. 20, 2021

(65) Prior Publication Data

US 2021/0346189 A1 Nov. 11, 2021

Related U.S. Application Data

(63) Continuation-in-part of application No. 16/188,965, filed on Nov. 13, 2018, now abandoned.

(51) Int. Cl.
*A61F 5/41* (2006.01)
*A63B 21/065* (2006.01)

(52) U.S. Cl.
CPC .............. *A61F 5/41* (2013.01); *A63B 21/065* (2013.01); *A61F 2005/412* (2013.01)

(58) Field of Classification Search
CPC ............................ A61F 5/41; A61F 2005/411; A61F 2005/412; A61F 2005/414
USPC .......................................................... 600/38
See application file for complete search history.

(56) References Cited

U.S. PATENT DOCUMENTS

| | | | | |
|---|---|---|---|---|
| 5,243,968 A | * | 9/1993 | Byun | A61H 19/32 600/38 |
| 8,382,656 B1 | * | 2/2013 | Brown | A61F 5/41 600/38 |
| 2004/0077970 A1 | * | 4/2004 | Osbon | A61B 50/30 600/562 |
| 2007/0093687 A1 | * | 4/2007 | Hoefer | A61F 5/41 600/41 |

* cited by examiner

*Primary Examiner* — Samuel G Gilbert
(74) *Attorney, Agent, or Firm* — The Thornton Firm, LLC

(57) ABSTRACT

An erectile dysfunction treatment system and method of use comprises a kit having a medical-grade plastic main cylinder having a proximal end and a distal end; three angled medical-grade plastic proximal end attachments, the medical-grade plastic proximal end attachments having a zero, forty-five and ninety degree angle, with each angled medical grade plastic proximal end having a fitted opening, the fitted opening capable of creating a sealing flange configured to be sealably held against the pubic area immediately surrounding a penis with the opposite end being attachable to the proximal end of the medical-grade plastic main cylinder; at least one medical-grade plastic weighted distal end attachment, the medical-grade plastic weighted distal end attachment being attachable to the medical-grade plastic main cylinder opposite to the proximal end; and at least one vacuum line attachment and quick release valve connected to the main cylinder.

17 Claims, 8 Drawing Sheets

ERECTILE DYSFUNCTION TREATMENT SYSTEM AND METHOD

CROSS-REFERENCE TO RELATED APPLICATIONS

The present continuation-in-part patent application claims priority benefit of the U.S. nonprovisional application for patent Ser. No. 16/188,965 titled "Erectile Dysfunction Treatment System and Method" filed on Nov. 13, 2018 under 35 U.S.C. 120. The contents of this related application are incorporated herein by reference for all purposes to the extent that such subject matter is not inconsistent herewith or limiting hereof.

RELATED CO-PENDING U.S. PATENT APPLICATIONS

Not applicable.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

BACKGROUND OF THE INVENTION

1. Field of the Invention

One or more embodiments of the invention generally relate to erectile dysfunction treatment systems. More particularly, embodiments of the invention relate to an improved penile enhancement apparatus and method of use that involves the use of both vacuum and distraction techniques to increase blood flow to and add both length and girth to the penis.

2. Description of the Related Art

Male erectile dysfunction is a common medical problem. It has many roots both physiological and psychological, but its effect may be devastating for both the individual and the individual's partner. Erectile dysfunction and/or penile shortening can result from common aging to surgical procedures such as radical prostatectomy and transurethral resection of the prostate.

Peyronie's disease (PD) is a connective tissue disorder involving the tunica albuginea layer of the penis. The fibrotic process that occurs may result in the formation of plaque, one of the classic findings on physical examination of the patient. Men afflicted by this disorder may present with pain, deformity (such as penile curvature or penile shortening) and/or erectile dysfunction (ED).

Several methods of treatment for erectile dysfunction are now in use ranging from drug therapy to the use of medical devices. In addition to erectile dysfunction treatment, many males wish to enhance their penis size and sexual performance, to which analogous treatments are available.

Among the more extreme methods of erectile dysfunction treatment is the use of relatively stiff flexible rods surgically implanted in the penis. Another extreme method is the implantation of slim tubular balloons in the penis rather than rods which may be inflated with fluid from a reservoir when an erection is desired. Though proven effective, these methods of treatment come with serious risks which deter numerous men from seeking such treatment.

Among the more conventional medical treatment devices commonly used, vacuum enlargement pumps have been known in the art for many years. The manner in which such pumps work is by placing a chamber over a flaccid penis and evacuating the chamber. The evacuation causes a pressure differential between the inside and outside of the chamber. This reduced pressure induces the penis to fill with blood and become erect. Erections may be maintained through the use of constriction bands which prevents blood from leaving the engorged and erect penis.

Most vacuum enlargement pump systems commonly known in the art comprise a chamber having a diaphragm at a lower end thereof and a tube attached at an upper end thereof. The tube is connected to a hand-held vacuum pump device which is usually in the form of an inflatable bulb or a trigger-style having a non-return valve therein. In use, a user places the penis through the diaphragm into the chamber and removes air from the chamber by use of the pump.

Penile traction devices are another medical device for treating erectile dysfunction and for increasing penile length. These devices usually consist of a plastic support ring, a silicone band, and two dynamic rods. Penile traction therapy works by holding the penis in a cradle and subjecting it to gentle and progressive traction forces that can be achieved by the addition of small metal extensions to the dynamic rods and cradle frame every few weeks. As the penile tissues are slowly yet surely stretched, which causes microscopic tears which, in theory, the body heals by producing cells to repair the gap. With each repair phase, the penile tissues expand. The desired end result being that the penis lengthens and widens and produces firmer and longer-lasting erections.

Both penile vacuum enlargement pumps and penile traction devices have limitations though. Most vacuum enlargement pumps have a standard, flat end for insertion of the penis which, when vacuum is applied, may cause discomfort or tissue damage to the penile area. When allowed to hang freely, most vacuum enlargement pumps will compress sensitive areas such as the testicles. Penile traction therapy is generally uncomfortable and requires a user to wear an uncomfortable device for many uses over a period of months to achieve any noticeable results. Presently, there exists a need for a more versatile male erectile dysfunction treatment system and method which provides the benefits of vacuum enlargement pump therapy and penile traction therapy.

SUMMARY

The present invention introduces a new technology, which overcomes the limitations of vacuum enlargement pumps and penile traction devices. The erectile dysfunction treatment system and method is versatile and readily implementable to treat a wide variety of erectile dysfunction problems and may serve to enhance penis length and girth.

In the preferred embodiment of the present invention, the erectile dysfunction treatment system comprises a kit having a medical-grade plastic main cylinder having a proximal end and a distal end; three angled medical-grade plastic proximal end attachments, the medical-grade plastic proximal end attachments having a zero, forty-five and ninety degree angle, with each angled medical grade plastic proximal end having a fitted opening, the fitted opening capable of creating a sealing flange configured to be sealably held against the pubic area immediately surrounding a penis with the opposite end being attachable to the proximal end of the medical-grade plastic main cylinder; at least one medical-grade plastic weighted distal end attachment, said medical-grade plastic weighted distal end attachment being attachable to the medical-grade plastic main cylinder opposite to the proximal end; and at least one vacuum line attachment and quick release valve connected to the main cylinder.

In embodiments of the present invention, a vacuum pump assembly may be detachably affixed to the main cylinder in more than one way, so that when attached and connected with a length of tubing, the pump assembly may be easily worked with the weighted distal end attached to the main cylinder. The present invention is intended to be used with numerous pumps available on the market. This feature provides two operational attributes in one device, both a vacuum device and a traction device.

Use of the erectile dysfunction treatment system may involve choosing a unit with a desirable angled proximal end or choosing an attachable proximal end, the proximal end having a varying angle for the penis to easily fit in the device while providing extra clearance for sensitive areas in the pubic region such as the testicles. In some embodiments, an attachable proximal end may attach to a main cylinder by various such as, but not limited to, a threaded screw mechanism. In other embodiments of the present invention, the proximal end and the main cylinder may be one single, contiguous unit with custom angles for use by patients with varying needs. In embodiments of the invention, the user may also choose an attachable and weighted distal end, which attaches to the opposite end of the main cylinder as the proximal end. The user then applies a vacuum to the system with a standard hand-held vacuum pump. Once a vacuum has been applied, the evacuated device is allowed to freely hang with the weighted distal end applying traction to the penis. In alternative embodiments of the invention, the evacuated device may be used at differing angles. The evacuated and weighted system may be applied for a therapeutic amount of time which the user may end by simply allowing air to enter the system.

BRIEF DESCRIPTION OF THE DRAWINGS

The invention directed by way of example, and not by way of limitation, in the figures of the accompanying drawings and in which like reference numerals refer to similar elements and in which.

Figure 1:
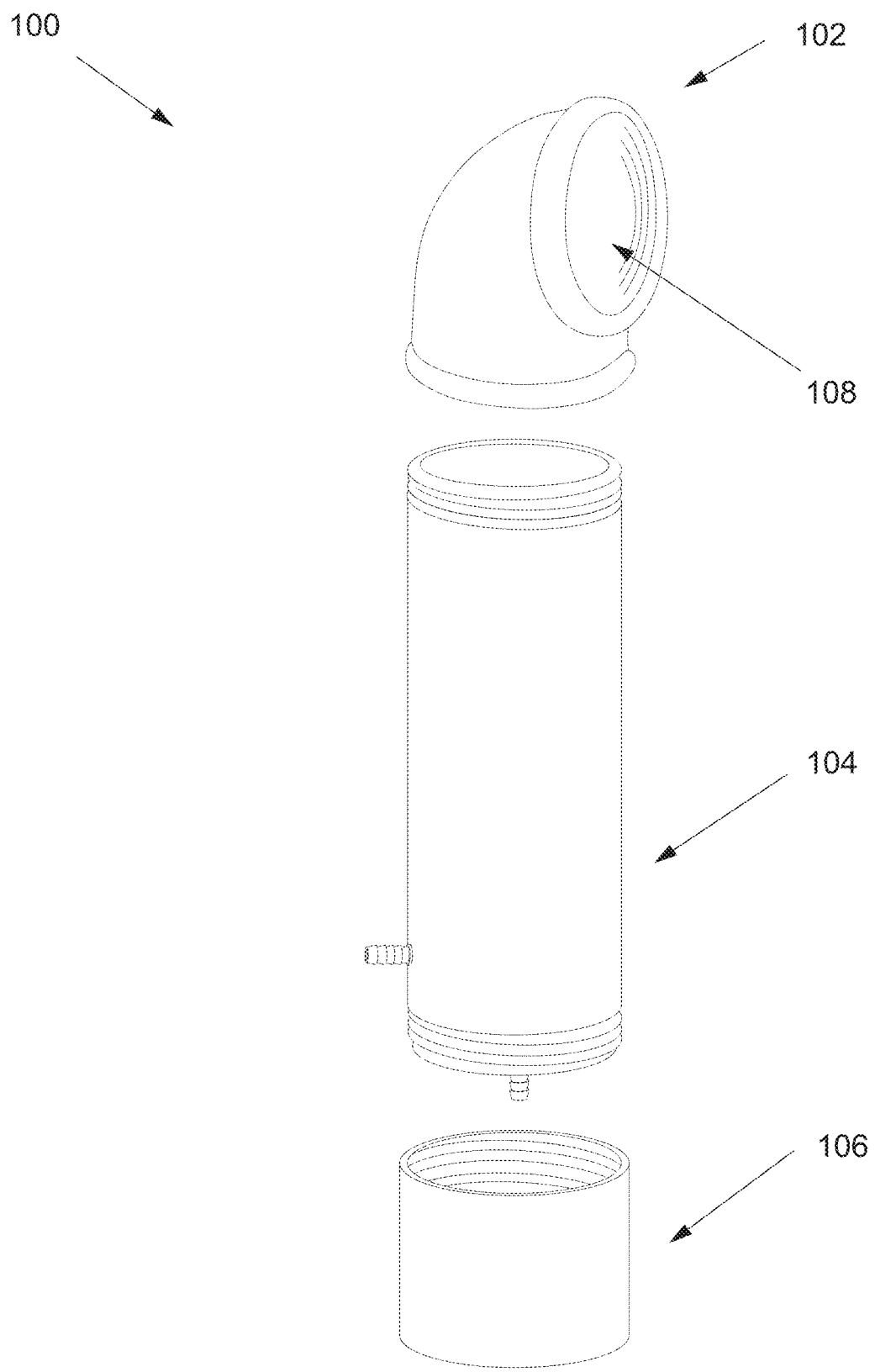
FIG. 1 is an exploded perspective view of the exemplary erectile dysfunction treatment system in accordance with an embodiment of the invention.

Unless otherwise indicated illustrations in the figures are not necessarily drawn to scale.

DETAILED DESCRIPTION OF THE PREFERRED EMBODIMENTS

Terminology used herein is used for the purpose of describing particular embodiments only, and is not intended to limit the scope of the present invention. It must be understood that as used herein and in the appended claims, the singular forms "a," "an," and "the" include the plural reference unless the context clearly dictates otherwise. For example, a reference to "an element" is a reference to one or more elements and includes all equivalents known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Language that may be construed to express approximation should be so understood unless the context clearly dictates otherwise.

Unless defined otherwise, all technical and scientific terms used herein have the same meanings as commonly understood by a person of ordinary skill in the art to which this invention belongs. Preferred methods, techniques, devices, and materials are described. But any methods, techniques, devices, or materials similar or equivalent to those described herein may be used in the practice or testing of the present invention. Structures described herein should also be understood to refer to functional equivalents of such structures.

References to "one embodiment," "an embodiment," "an alternative embodiment," "various embodiments," etc., may indicate that the embodiment(s) of the invention so described may include particular features, structures, or characteristics. However, not every embodiment necessarily includes the particular features, structures, or characteristics. Further, repeated use of the phrase "in one embodiment," or "in an exemplary embodiment," do not necessarily refer to the same embodiment although they may. A description of an embodiment with several components in communication with each other does not imply that all such components are required. On the contrary, a variety of optional components are described to illustrate the wide variety of possible embodiments of the present invention.

As is well known to those skilled in the art, many careful considerations and compromises typically must be made when designing for the optimal manufacture of a commercial implementation of such an erectile dysfunction treatment system. A commercial implementation in accordance with the spirit and teachings of the invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art.

The exemplary erectile dysfunction treatment system and method will now be described in detail with reference to embodiments thereof as illustrated in the accompanying drawings.

FIG. 1 is an exploded perspective view of the exemplary erectile dysfunction treatment system in accordance with an embodiment of the invention. In one embodiment of the invention, the exemplary erectile dysfunction treatment system 100 comprises an attachable angled proximal end 102 with a fitted opening 108, a main cylinder 104, and a weighted attachable distal end 106. In one embodiment of the invention, the components attach to one another by a basic threaded screw method. Persons skilled in the art will readily appreciate that other mechanical means for attaching the components to one another may be used such as, but not limited to, a bayonet mount or other grooved fittings. In the preferred embodiment of the invention, the components are made of a clear, medical-grade polycarbonate resin plastic. However, persons skilled in the art will readily appreciate that alternative embodiments may be made from a number of materials such as, but not limited to, clear acrylic plastics, ABS plastic, polycarbonates, polyvinyl chloride (PVC), or various other plastic equivalents. The object is to provide a strong and rigid system which can withstand partial vacuums as well as to provide rigid surfaces which can be fitted for the efficient changing of components.

Figure 2:
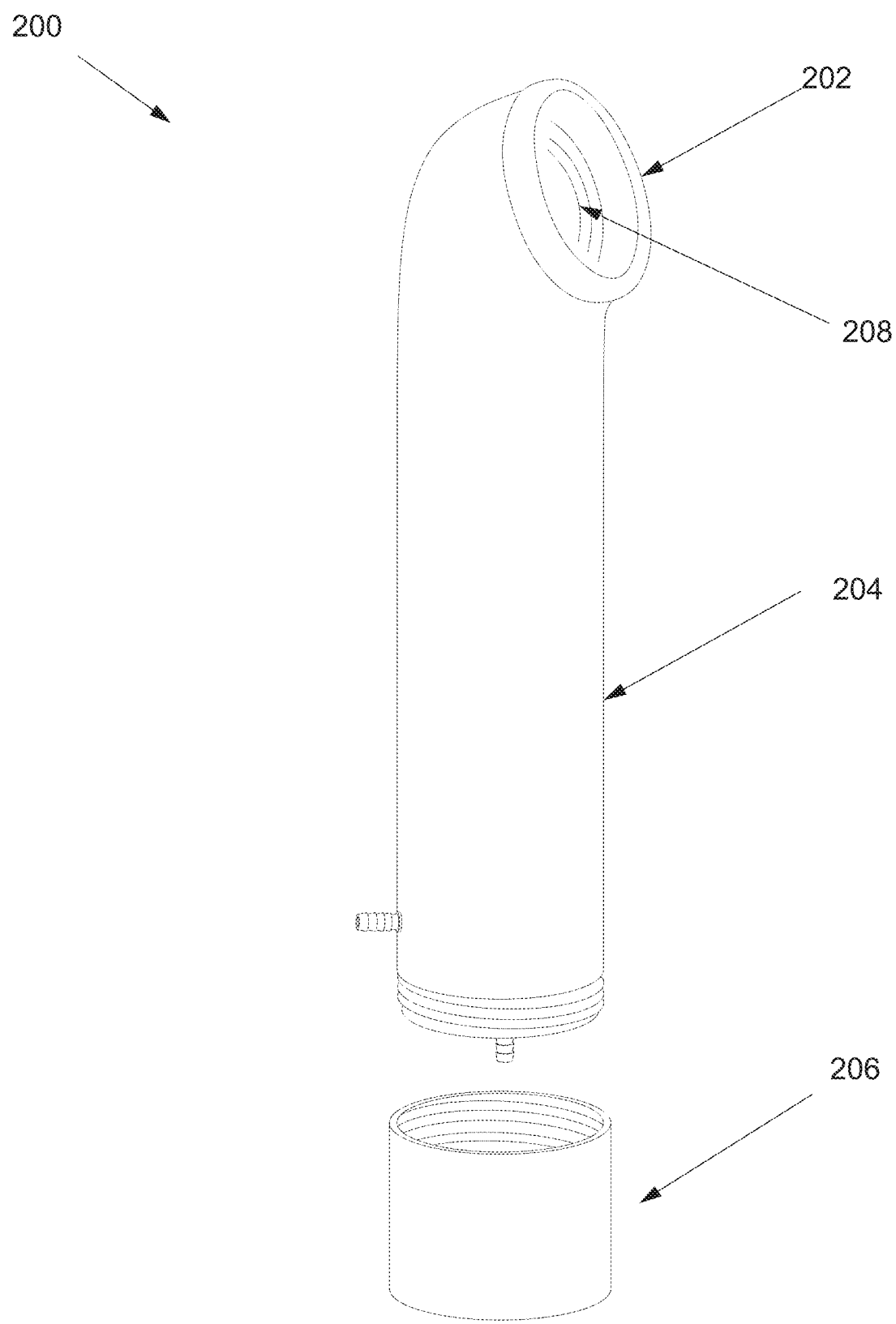
FIG. 2 is an exploded perspective view of the exemplary erectile dysfunction treatment system in accordance with an alternative embodiment of the invention.

FIG. 2 is an exploded perspective view of the exemplary erectile dysfunction treatment system in accordance with an alternative embodiment of the invention. In an alternative embodiment of the invention, the exemplary erectile dysfunction treatment system 200 comprises a main cylinder with an angled proximal end 202 with a fitted opening 206, and a weighted attachable distal end 204. In one embodiment of the invention, the components attach to one another by a basic threaded screw method. Persons skilled in the art will readily appreciate that other mechanical means for attaching the components to one another may be used such as, but not limited to, a bayonet mount or other grooved fittings. In another embodiment, the distal end may simply consist of an integrated distal end, thus making a single contiguous unit. As with the preferred embodiment of the invention, the components are made of a clear, medical-grade polycarbonate resin plastic. However, persons skilled in the art will readily appreciate that alternative embodiments may be made from a number of materials such as, but not limited to, clear acrylic plastics, ABS plastic, polycarbonates, polyvinyl chloride (PVC), or various other plastic equivalents.

Figure 3:
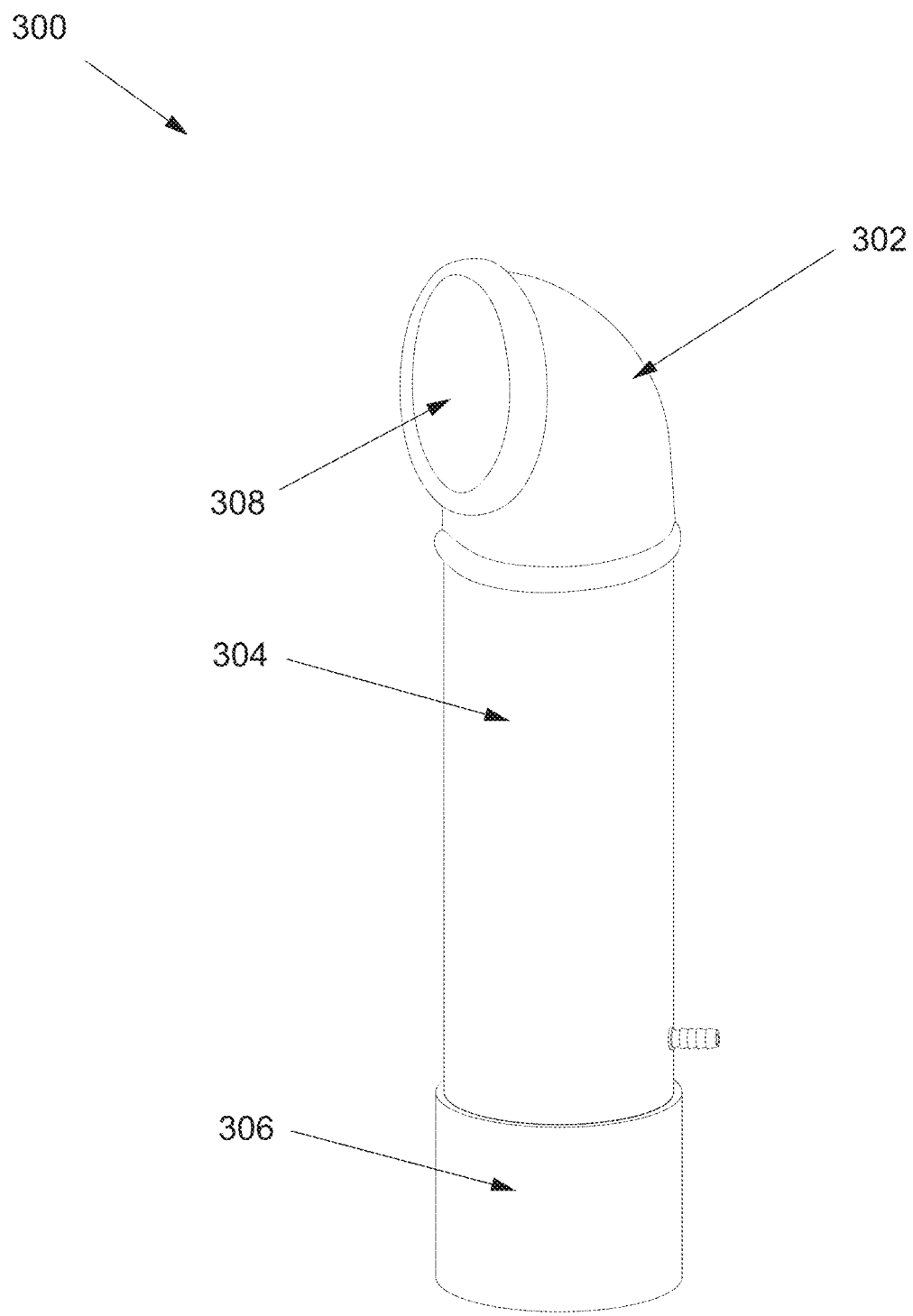
FIG. 3 is a perspective view of an assembled erectile dysfunction treatment system in accordance with an embodiment of the invention.

FIG. 3 is a perspective view of an assembled erectile dysfunction treatment system 300 in accordance with an embodiment of the invention. The invention is designed to provide the user with a smooth, near-contiguous interior so as to eliminate rough edges which may hurt highly innervated and sensitive tissues. In one embodiment of the invention, the erectile dysfunction treatment system 300 may be one single contiguous unit with the angled proximal end and weighted distal end as mere extensions of the main cylinder. In another embodiment of the invention, the angled proximal end may be an extension of the main cylinder with the weighted distal end being attachable to the main cylinder. In yet another embodiment of the invention, the angled proximal end may attach to the main cylinder with the distal end also attachable to the main cylinder.

Figure 4A:
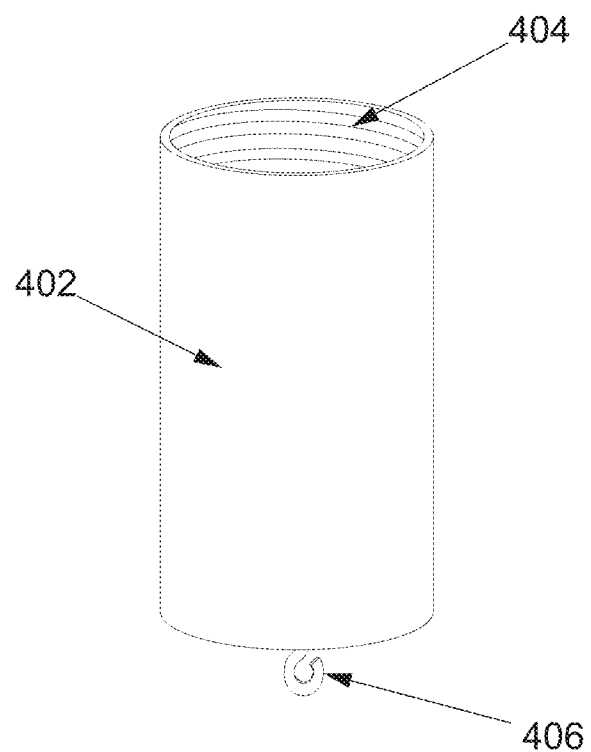
FIG. 4A is a perspective view of the attachable weighted distal end of the exemplary erectile dysfunction treatment system in accordance with an embodiment of the invention.

FIG. 4A is a perspective view of the attachable weighted distal end of the exemplary erectile dysfunction treatment system in accordance with an embodiment of the invention. In the preferred embodiment, the attachable weighted distal end is cylindrically shaped and made of a plastic housing 402 which may made of a clear, medical-grade polycarbonate resin plastic. However, persons skilled in the art will readily appreciate that alternative embodiments may be made from a number of materials such as, but not limited to, clear acrylic plastics, ABS plastic, polycarbonates, polyvinyl chloride (PVC), or various other plastic equivalents. The plastic attachable weighted distal end may be hollow with a fixed amount of a dense material added to create a fixed weight for distraction therapy. Alternative embodiments may assume different shapes, and may be made from other materials such as, but not limited to, wood, metal or stone. In one embodiment of the invention, the weighted distal end attaches to the end of the main cylinder by a basic threaded screw method with the female threaded component 404 located on one end. In embodiments of the invention, weighted distal end attachments can attach to one another by various attachment means such as, but not limited to, a simple screw mechanism. By allowing a user to create different weighted attachments, the exemplary erectile dysfunction treatment system can perform a number of treatment combinations and functions. Persons skilled in the art will readily appreciate that other mechanical means for attaching the components to one another may be used such as, but not limited to, a bayonet mount or other grooved fittings. On the opposite end, numerous accessories 406 may be attached. In this view, a utility hook for hanging extra weight is depicted. However, in other embodiments of the invention, accessories such as, but not limited to, loops, lights, pump mounts, battery mounts may be attached. In an alternative embodiment of the invention, the opposite end of the distal end may also be threaded so as to accommodate additional weighted units to create a greater distractive force when in use.

Figure 4B:
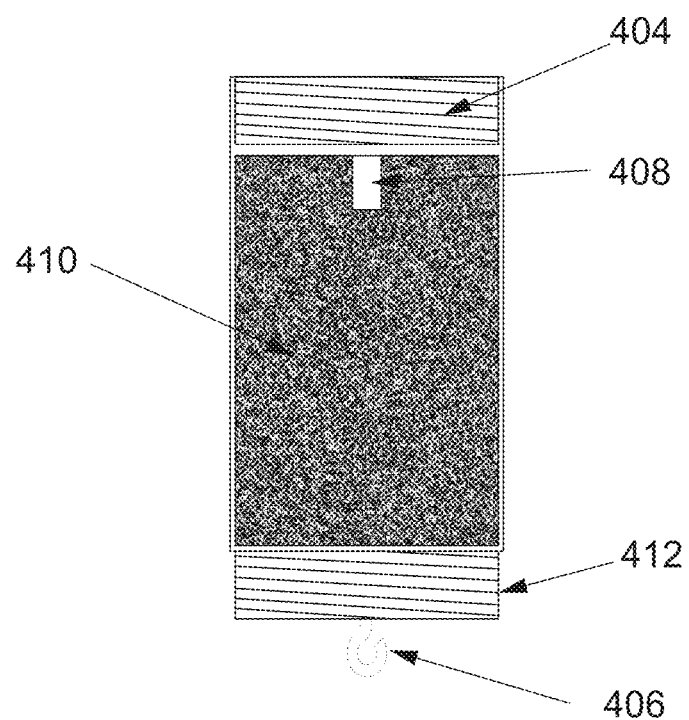
FIG. 4B is a side sectional view of the attachable weighted distal end of the exemplary erectile dysfunction treatment system in accordance with an embodiment of the invention.

FIG. 4B is a side sectional view of the attachable weighted distal end of the exemplary erectile dysfunction treatment system in accordance with an embodiment of the invention. In the sectional view, a housing for a vacuum pump line attachment 408 is provided. In one embodiment of the invention, the weighted distal end attaches to the end of the main cylinder by a basic threaded screw method with the female threaded component 404 located on one end. On the opposite end, numerous accessory attachment means 406 may be attached. Persons skilled in the art will readily appreciate that other mechanical means for attaching the components to one another may be used such as, but not limited to, a bayonet mount or other grooved fittings. The plastic weighted distal end may be hollow with a fixed amount of ballast 410 which may be added to the space inside the plastic housing. Persons skilled in the art will readily appreciate that the ballast may consist of a dense material such as, but not limited to, iron, iron alloy or lead. In other embodiments, the ballast may consist of water with an inlet at the opposite end of the threaded component where the accessory hook is depicted. In an embodiment of the invention, the opposite end of the distal end may also be threaded 412 so as to accommodate additional weighted units to create a greater distractive force when in use.

Figure 5A:
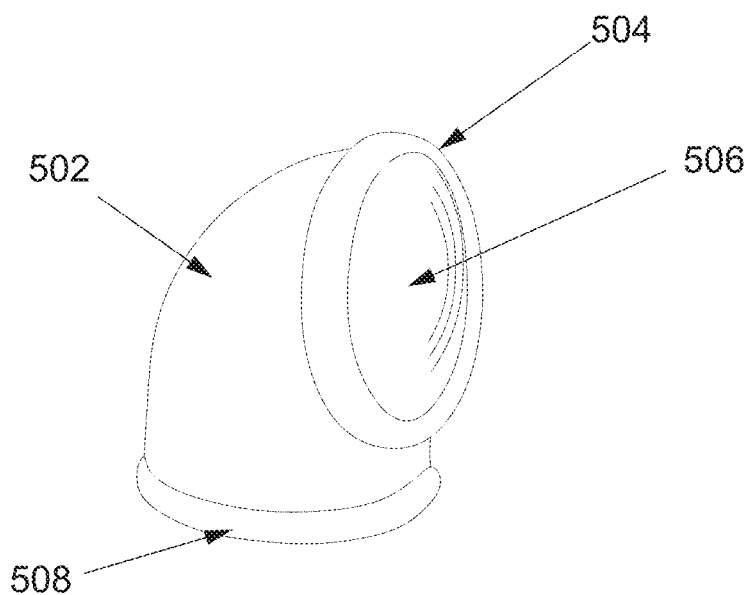
FIG. 5A is a perspective view of the attachable proximal end of the exemplary erectile dysfunction treatment system in accordance with an embodiment of the invention.

FIG. 5A is a perspective view of the attachable proximal end of the exemplary erectile dysfunction treatment system in accordance with an embodiment of the invention. In the preferred embodiment, the attachable angled proximal end is cylindrically shaped, yet angled, and made of a plastic housing 502 which may made of a clear, medical-grade polycarbonate resin plastic. However, persons skilled in the art will readily appreciate that alternative embodiments may be made from a number of materials such as, but not limited to, clear acrylic plastics, ABS plastic, polycarbonates, polyvinyl chloride (PVC), or various other plastic equivalents. A sealing flange 504 may include a sealing constriction ring which is attachably mounted on the angled proximal end in the vicinity of the fitted opening 506, the sealing flange including a generally ring-shaped body having a circumferentially extending engagement formation for releasable sealing engagement with the angled proximal end in the vicinity of the fitted opening. In the preferred embodiment, the sealing flange 504 will be round shaped and circumferentially shaped the same as the edge of the angled end.

Figure 5B:
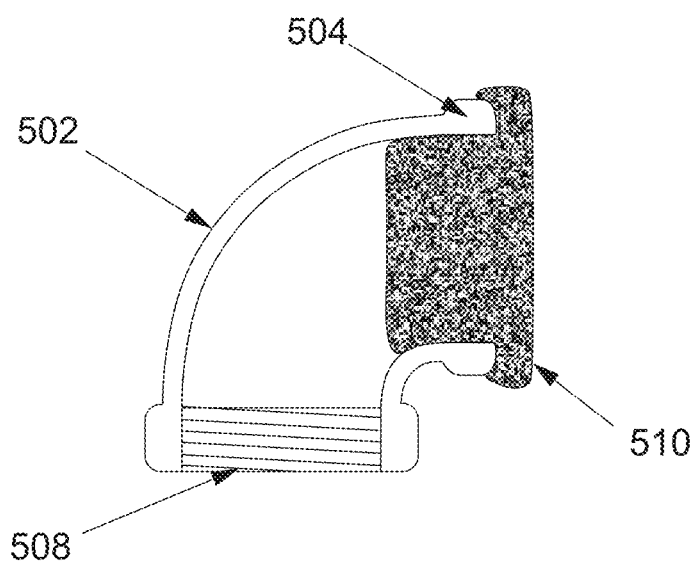
FIG. 5B is a side sectional view of the attachable weighted distal end of the exemplary erectile dysfunction treatment system in accordance with an embodiment of the invention.

FIG. 5B is a side sectional view of the attachable angled proximal end of the exemplary erectile dysfunction treatment system in accordance with an embodiment of the invention. In this view, the attachable angled proximal end is depicted as having a ninety-degree angle. However, in other embodiments of the present invention, the angle may vary. In one embodiment of the invention, a kit is provided with a forty-five degree angled proximal end attachment, a ninety-degree proximal end attachment, and a one-hundred and eighty degree attachment. In one exemplary embodiment, a kit is provided with ten-, twenty-, thirty-, forty-five, sixty- and ninety-degree attachments. The purpose of the angled attachments is to allow the user differing angles of distraction therapy coupled with preventing painful stress on the testicles and other sensitive areas. An inner sleeve 510 may be attachable to the sealing flange 504 and may assume numerous configurations designed for numerous purposes such as, but not limited to, blood flow constriction and sexual stimulation. The inner sleeve 510 may be made from numerous materials such as, but not limited to, latex, rubber or silicone. In one embodiment of the invention, the angled proximal end attaches to the end of the main cylinder by a basic threaded screw method with the female threaded component 508 located on one end. Persons skilled in the art will readily appreciate that other mechanical means for attaching the components to one another may be used such as, but not limited to, a bayonet mount or other grooved fittings.

Figure 5C:
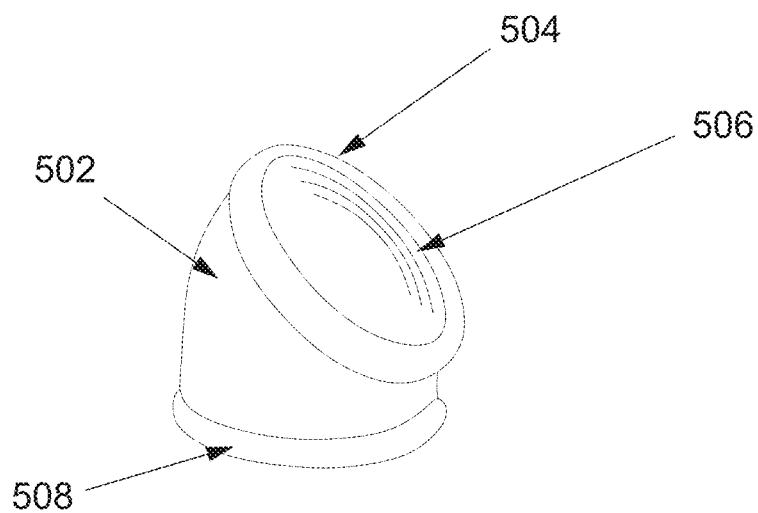
FIG. 5C is a perspective view of the attachable proximal end of the exemplary erectile dysfunction treatment system in accordance with an embodiment of the invention.

FIG. 5C is a perspective view of the attachable proximal end of the exemplary erectile dysfunction treatment system in accordance with an embodiment of the invention. In the preferred embodiment, the attachable angled proximal end is cylindrically shaped, yet angled, and made of a plastic housing 502 which may made of a clear, medical-grade polycarbonate resin plastic. However, persons skilled in the art will readily appreciate that alternative embodiments may be made from a number of materials such as, but not limited to, clear acrylic plastics, ABS plastic, polycarbonates, polyvinyl chloride (PVC), or various other plastic equivalents. A sealing flange 504 may include a sealing constriction ring which is attachably mounted on the angled proximal end in the vicinity of the fitted opening 506, the sealing flange including a generally ring-shaped body having a circumferentially extending engagement formation for releasable sealing engagement with the angled proximal end in the vicinity of the fitted opening. In the preferred embodiment, the sealing flange 504 will be round shaped and circumferentially shaped the same as the edge of the angled end.

Figure 5D:
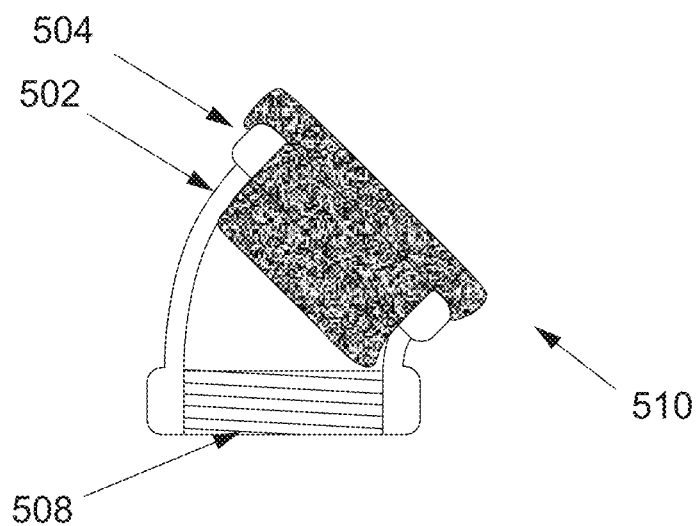
FIG. 5D is a side sectional view of the attachable weighted distal end of the exemplary erectile dysfunction treatment system in accordance with an embodiment of the invention.

FIG. 5D is a side sectional view of the attachable angled proximal end of the exemplary erectile dysfunction treatment system in accordance with an embodiment of the invention. In this view, the attachable angled proximal end is depicted as having a forty-five-degree angle. However, in other embodiments of the present invention, the angle may vary. In one embodiment of the invention, a kit is provided with a forty-five degree angled proximal end attachment, a ninety-degree proximal end attachment, and a one-hundred and eighty degree attachment. In one exemplary embodiment, a kit is provided with ten-, twenty-, thirty-, forty-five, sixty- and ninety-degree attachments. The purpose of the angled attachments is to allow the user differing angles of distraction therapy coupled with preventing painful stress on the testicles and other sensitive areas. An inner sleeve 510 may be attachable to the sealing flange 504 and may assume numerous configurations designed for numerous purposes such as, but not limited to, blood flow constriction and sexual stimulation. The inner sleeve 510 may be made from numerous materials such as, but not limited to, latex, rubber or silicone. In one embodiment of the invention, the angled proximal end attaches to the end of the main cylinder by a basic threaded screw method with the female threaded component 508 located on one end. Persons skilled in the art will readily appreciate that other mechanical means for attaching the components to one another may be used such as, but not limited to, a bayonet mount or other grooved fittings.

Figure 6:
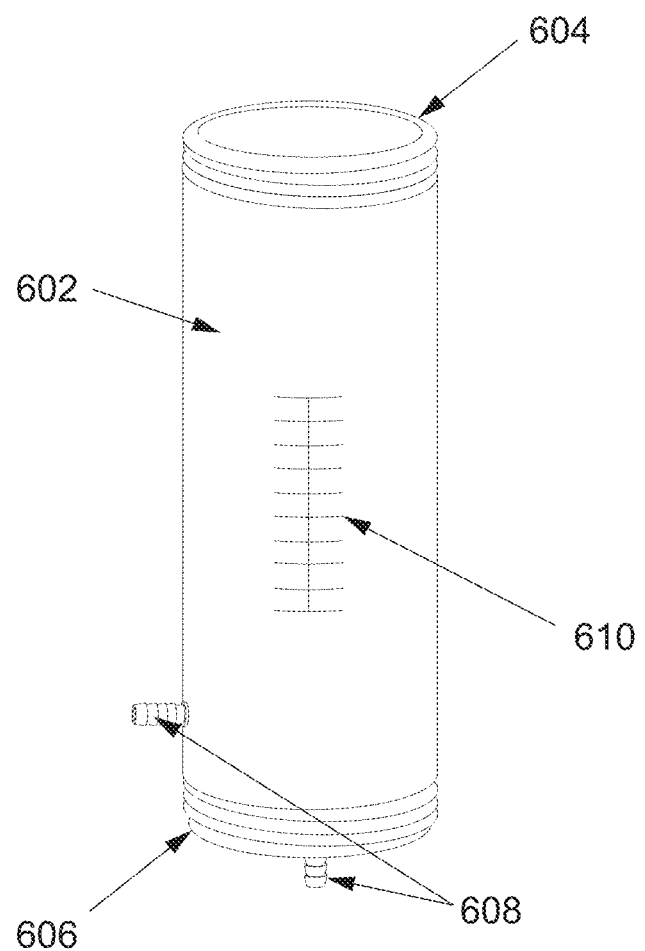
FIG. 6 is a perspective view of the main cylinder of the exemplary erectile dysfunction treatment system in accordance with an embodiment of the invention.

FIG. 6 is a perspective view of the main cylinder of the exemplary erectile dysfunction treatment system in accordance with an embodiment of the invention. The main cylinder consists of a body 602, a proximal end 604 and a distal end 606. In this view, the proximal and distal ends of the main cylinder have threaded ends which the attachable angled proximal end may attach to the proximal end 604 and the attachable weighted distal end may attach to the distal end 606. The length of the main cylinder may vary to accommodate differing therapeutic needs of users of the system. Persons skilled in the art will readily appreciate that other mechanical means for attaching the components to one another may be used such as, but not limited to, a bayonet mount or other grooved fittings. Vacuum line attachments 608 are located at the distal end of the main cylinder and on the sidewall of the main cylinder body 602. Visual aids such as graduations 610 may be located on the outer sidewall of the main cylinder body. In the preferred embodiment, the main cylinder is made of a plastic housing 602 which may made of a clear, medical-grade polycarbonate resin plastic. However, persons skilled in the art will readily appreciate that alternative embodiments may be made from a number of materials such as, but not limited to, clear acrylic plastics, ABS plastic, polycarbonates, polyvinyl chloride (PVC), or various other plastic equivalents.

In an embodiment of the present invention, a vacuum pump assembly may be detachably affixed to the main cylinder in more than one way, so that when attached and connected with a length of tubing, the pump assembly may be easily worked with the weighted distal end attached to the main cylinder. This feature provides two operational attributes in one device, both a vacuum device and a traction device. Persons skilled in the art will readily appreciate that there are several types of vacuum pump assemblies which may be used with various embodiments of the present invention. In addition, persons skilled in the art will readily understand that varying therapeutic pressures may be applied and achieved through using differing vacuum pump assemblies known and appreciated in the art. In the present view, the vacuum line attachments 606 are depicted as standard vacuum hose attachments where a vacuum pump assembly serves as the one-way valve. However, in other embodiments of the invention, various check valves well known in the art may be attached to and extend from the main cylinder. In other embodiments of the invention, a valved male threaded coupling body may be used. Persons skilled in the art will understand that the vacuum line attachments 606 are designed to incorporate a quick release valve mechanism whether it be incorporated in the pump assembly or in the main cylinder pump attachments.

Figure 7:
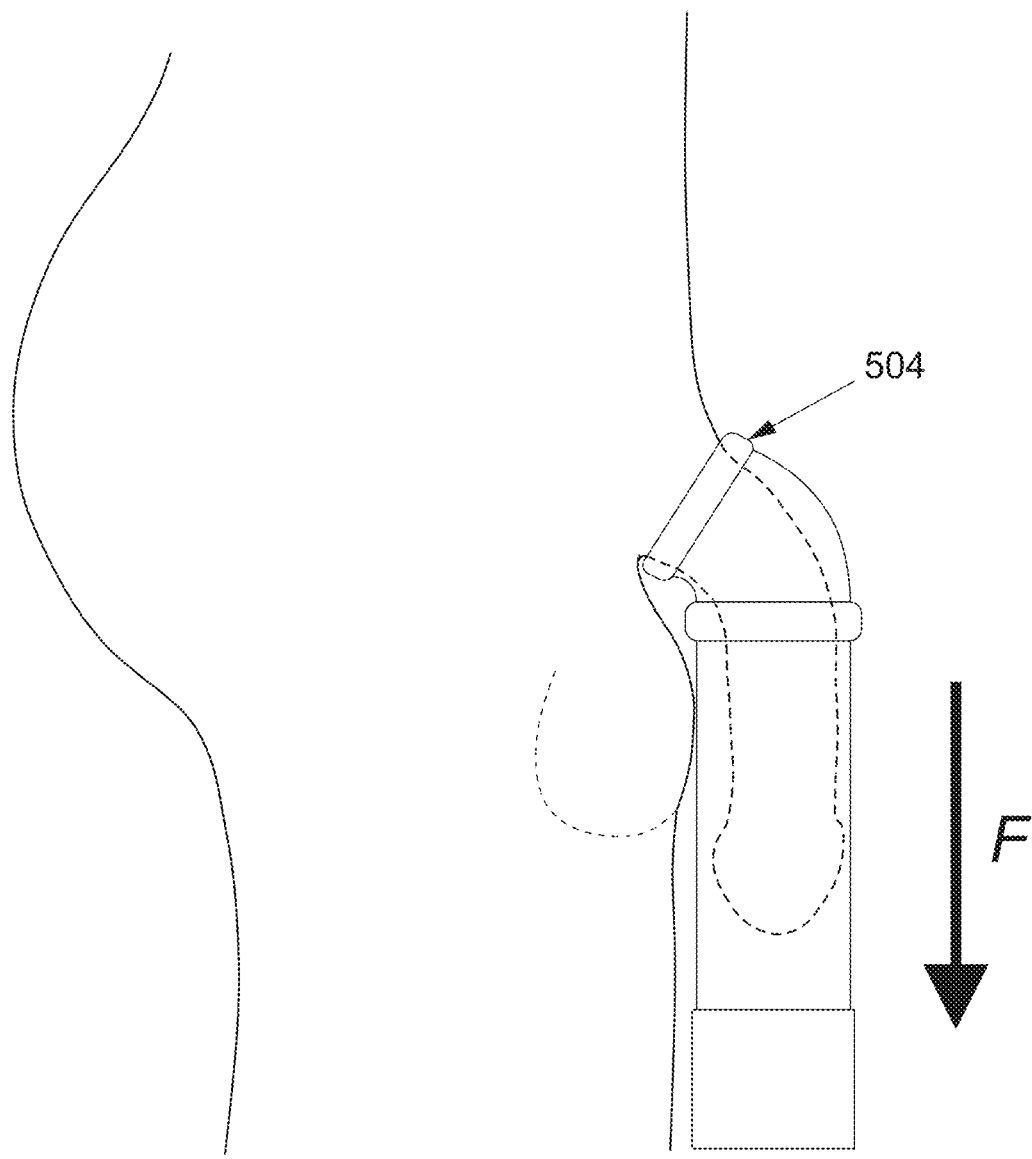
FIG. 7 is a side view of a person using the exemplary erectile dysfunction treatment system in accordance with an embodiment of the invention.

FIG. 7 is a side view of a person using the exemplary erectile dysfunction treatment system in accordance with an embodiment of the invention. In this view, the user has inserted the penis into the angled proximal end. As illustrated, the main cylinder has been evacuated of air through a vacuum line attached to and then removed from the vacuum line attachments. Also illustrated in this view, the angled proximal end allows for the exemplary erectile dysfunction treatment system to hang freely when a vacuum has been applied while not placing pressure on other sensitive areas such as the testicles. A therapeutic distractive force F is applied to the penis by allowing the sealed and evacuated system to freely hang while the user is standing, seated or in a position where the weight of the distal end may apply a distractive force on the penis. In other uses, a user may use the system in different positions such as, but not limited to, sitting, standing or laying supine. Persons skilled in the art will readily appreciate that the use of the exemplary erectile dysfunction treatment system affords the users numerous different treatment options through the use of angled proximal ends and weighted distal ends.

The exemplary erectile dysfunction treatment system operates differently than conventional pump systems in that the angled proximal end is designed to minimize pressure around the penile area. Prior to insertion, the penis and pubic area may be prepared for attaching the exemplary erectile dysfunction treatment system. In one example, the pubic area and penis are coated with a water-soluble lubricant to form a better seal and to provide for additional stimulation. In other methods, constriction bands or other enhancements can be used. A vacuum pump line or lines are then connected to the vacuum line attachments. The angled proximal end is held against the pubic area immediately surrounding the penis so as to generally form a seal when a vacuum is applied. The lipped nature of the sealing flange 504 assists in forming the seal. In alternative embodiments of the invention, a custom fitted sleeve having an outer diameter, an inner diameter, and a sealing interface capable of creating an airtight seal against the pubic area surrounding a penis is insertable into the fitted opening of each of the angled medical-grade plastic proximal ends which sealably attaches to the sealing flange 504 and may assume numerous configurations and conformations designed for various purposes such as, but not limited to, formation of a tighter seal, blood flow constriction, and sexual stimulation. A partial vacuum is then created in the interior of the main cylinder by the user grasping a hand vacuum pump and gripping the vacuum pump in a repeated action. In other embodiments, an electric vacuum pump may be used.

Creation of a partial vacuum in the vacuum cylinder results in the application of an external negative pressure to the penis which results in filling of the penile erectile tissues with blood. As the penile tissues are filled with blood, the penis expands in length and girth and becomes rigid. Should discomfort result from the creation of the partial vacuum, the user may reduce the partial vacuum by operating a valve mechanism to a level which is comfortable. The user may also easily remove the device should discomfort continue. Once the user achieves a satisfactory result, a constriction ring may be placed around the base of the penis to maintain the penile rigidity. In the preferred embodiment, a pressure adjust valve is used to regulate the vacuum. Persons skilled in the art will readily appreciate that a standard hand-held vacuum pump that is self-sealing such that upon release of the pressure adjust valve, the main cylinder will equilibrate with atmospheric pressure. In alternative embodiments of the invention, warm water or other fluids may be added into the erectile dysfunction treatment system and a partial vacuum created by applying a pump to evacuate the water from the system thus creating a different vacuum effect.

The invention includes a method of treating erectile dysfunction and related problems using the exemplary erectile dysfunction treatment kit having a medical-grade plastic main cylinder having a proximal end and a distal end, three angled medical-grade plastic proximal end attachments, said medical-grade plastic proximal end attachments having forty-five, ninety and one hundred and eighty degree angles, with each angled medical grade plastic proximal end having a fitted opening, each fitted opening configured to be sealably held against the pubic area immediately surrounding a penis and the opposite end being attachable to the proximal end of the said medical-grade plastic main cylinder, at least one medical-grade plastic weighted distal end attachment, said medical-grade plastic weighted distal end attachment being attachable to the medical-grade plastic main cylinder opposite to the proximal end; and at least one vacuum line attachment connected to the main cylinder. As shown in FIG. 7, this method includes the steps of a user selecting an angled proximal end for use; a user attaching the said angled proximal end to the main cylinder; a user selecting a weighted distal end; a user attaching the said weighted distal end to the main cylinder; a user preparing the pubic area for attaching the erectile dysfunction treatment kit; a user placing a penis through the fitted opening of the attached proximal end into the main cylinder; a user creating a partial vacuum inside the assembled angled proximal end and main cylinder; a user allowing the attached erectile dysfunction kit to apply distractive force on the pubic area including a penis for a recommended therapeutic amount of time; and a user releasing the said partial vacuum from inside the assembled angled proximal end and main cylinder.

The invention further includes a method of treating erectile dysfunction and related problems using the exemplary erectile dysfunction treatment kit having a medical-grade plastic main cylinder having a proximal end and a distal end, with the main cylinder's proximal end having forty-five, ninety and one hundred and eighty degree angles, with each angled medical grade plastic proximal end having a fitted opening, each fitted opening configured to be sealably held against the pubic area immediately surrounding a penis and the opposite end being attachable to the proximal end of the said medical-grade plastic main cylinder, at least one medical-grade plastic weighted distal end attachment, said medical-grade plastic weighted distal end attachment being attachable to the medical-grade plastic main cylinder opposite to the proximal end; and at least one vacuum line attachment connected to the main cylinder. The method includes the steps of a user creating an erectile dysfunction treatment system by selecting an angled proximal end for use, attaching the said angled proximal end to the main cylinder, selecting a weighted distal end and attaching the said weighted distal end to the main cylinder; a user preparing the pubic area for attaching the erectile dysfunction treatment system; a user placing a penis through the fitted opening of the attached proximal end into the main cylinder; a user creating a partial vacuum inside the attached proximal end; and a user manipulating the attached erectile dysfunction treatment system by grasping the said attached erectile dysfunction treatment system by holding the attached erectile dysfunction treatment system at different angles for a recommended amount of time and applying a distractive force to the attached erectile dysfunction treatment system by pulling the said attached erectile dysfunction treatment system in a direction away from the pubic area; and a user releasing the said partial vacuum from inside the assembled angled proximal end and main cylinder. The holding of the system at differing angles for a recommended amount of time and pulling the system away from the pubic area applies a distractive force on the base of the penis which can correct certain erectile dysfunction problems such as Peyronie's Disease and add length to a penis. This holding at different angles of the angled proximal end of the exemplary erectile dysfunction treatment system and pulling the erectile dysfunction treatment system away from the pubic area while the system is attached through a partial vacuum to the pubic area produces unique results.

The invention further includes a method of treating erectile dysfunction and related problems using the exemplary erectile dysfunction treatment kit having a medical-grade plastic main cylinder having a proximal end and a distal end, three angled medical-grade plastic proximal end attachments, said medical-grade plastic proximal end attachments having forty-five, ninety and one hundred and eighty degree angles, with each angled medical grade plastic proximal end having a fitted opening, each fitted opening configured to be sealably held against the pubic area immediately surrounding a penis and the opposite end being attachable to the proximal end of the said medical-grade plastic main cylinder, at least one medical-grade plastic weighted distal end attachment, said medical-grade plastic weighted distal end attachment being attachable to the medical-grade plastic main cylinder opposite to the proximal end; and at least one vacuum line attachment connected to the main cylinder. The method includes the steps of a user creating an erectile dysfunction treatment system by selecting an angled proximal end for use, attaching the said angled proximal end to the main cylinder, selecting a weighted distal end and attaching the said weighted distal end to the main cylinder; a user preparing the pubic area for attaching the erectile dysfunction treatment system; a user placing a penis through the fitted opening of the attached proximal end into the main cylinder; a user creating a partial vacuum inside the attached proximal end; and a user manipulating the attached erectile dysfunction treatment system by grasping the said attached erectile dysfunction treatment system by holding the attached erectile dysfunction treatment system at different angles for a recommended amount of time and applying a distractive force to the attached erectile dysfunction treatment system by pulling the said attached erectile dysfunction treatment system in a direction away from the pubic area; and a user releasing the said partial vacuum from inside the assembled angled proximal end and main cylinder. The holding of the system at differing angles for a recommended amount of time and pulling the system away from the pubic area applies a distractive force on the base of the penis which can correct certain erectile dysfunction problems such as Peyronie's Disease and add length to a penis. This holding at differing angles of the angled proximal end of the exemplary erectile dysfunction treatment system and pulling the erectile dysfunction treatment system away from the pubic area while the system is attached through a partial vacuum to the pubic area produces unique results.

The aforementioned methods of treatment can include the steps of adding additional weight to the weighted distal end of the system. Furthermore, the aforementioned methods of treatment can include the step of inserting a custom fitted sleeve having an outer diameter, an inner diameter, and a sealing interface capable of creating an airtight seal against the pubic area surrounding a penis into the fitted opening of the selected the angled medical-grade plastic proximal ends, with the said outer diameter of the custom fitted sleeve configured to be seated around the sealing flange. Finally, each of the aforementioned methods of use can include the step of changing the angled proximal end attachments.

Having fully described at least one embodiment of the exemplary male erectile dysfunction treatment system and method, other equivalent or alternative methods of implementing the male erectile dysfunction treatment system and method according to the present invention will be apparent to those skilled in the art. Various aspects of the invention have been described above by way of illustration, and the specific embodiments disclosed are not intended to limit the invention to the particular forms disclosed. The particular implementation of the male erectile dysfunction treatment system and method may vary depending upon the particular context or application.

By way of example, and not limitation, the erectile dysfunction treatment system and method described in the foregoing patent application is principally directed towards using a standard hand-held vacuum pump. However, similar techniques may instead be applied to electric vacuum pumps, fluid-based systems or specialty enlargement systems, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Although specific features of the invention are shown in some drawings and not others, persons skilled in the art will understand that this is for convenience. Each feature may be combined with any or all of the other features in accordance with the invention. The words "including," "comprising," "having," and "with" as used herein are to be interpreted broadly and comprehensively, and are not limited to any physical interconnection. Claim elements and steps herein may have been numbered and/or lettered solely as an aid in readability and understanding. Any such numbering and lettering in itself is not intended to and should not be taken to indicate the ordering of elements and/or steps in the claims to be added at a later date.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Any amendment presented during the prosecution of the application for this patent is not a disclaimer of any claim element presented in the description or claims to be filed. Persons skilled in the art cannot reasonably be expected to draft a claim that would literally encompass each and every equivalent.

The invention claimed is:

1. An erectile dysfunction treatment kit comprising:
   a. a medical-grade plastic main cylinder having a proximal end and a distal end;
   b. at least two angled medical-grade plastic proximal end attachments, said medical-grade plastic proximal end attachments having a forty-five and ninety degree angle, each angled medical grade plastic proximal end having a fitted opening, said fitted opening capable of creating a sealing flange and configured to be sealably held against an area immediately surrounding a penis, said angled medical-grade plastic proximal end attachments being attachable to the proximal end of the said medical-grade plastic main cylinder;
   c. at least one medical-grade plastic weighted distal end attachment, said medical-grade plastic weighted distal end attachment being attachable to the medical-grade plastic main cylinder opposite to the proximal end; and
   d. at least one vacuum line attachment and quick release valve connected to the main cylinder.

2. The erectile dysfunction treatment kit of claim 1 wherein each fitted opening of the at least two medical-grade plastic proximal end attachments, is configured to be held in place against the area immediately surrounding a penis so as to form a seal when a vacuum is applied.

3. The erectile dysfunction treatment kit of claim 1 wherein a custom fitted sleeve having an outer diameter, an inner diameter, and a sealing interface capable of creating an airtight seal against the area surrounding a penis is insertable into the fitted opening of each of the angled medical-grade plastic proximal ends, with the said outer diameter of the custom fitted sleeve configured to be seated around the fitted opening so as to create an airtight seal when a partial vacuum is applied.

4. The erectile dysfunction treatment kit of claim 3 wherein the inner diameter of the custom fitted sleeve is shaped to provide sexual stimulation to a user.

5. The erectile dysfunction treatment kit of claim 1 wherein additional medical-grade plastic weighted distal end attachments can be attached to the medical-grade plastic weighted distal end attachment.

6. The erectile dysfunction treatment kit of claim 1 further comprising an angled medical-grade plastic proximal end attachments, said medical-grade plastic proximal end attachments having a thirty-degree angle.

7. The erectile dysfunction treatment kit of claim 1 further comprising an angled medical-grade plastic proximal end attachments, said medical-grade plastic proximal end attachments having a sixty-degree angle.

8. The erectile dysfunction treatment kit of claim 1 wherein the at least one medical-grade plastic weighted distal end attachment is hollow with a fixed amount of a dense material added to create a fixed weight for distraction therapy.

9. The erectile dysfunction treatment kit of claim 1 further comprising an angled medical-grade plastic proximal end attachments, said medical-grade plastic proximal end attachments having a one hundred and eighty-degree angle.

10. A method of treating erectile dysfunction and related problems using an erectile dysfunction treatment kit having medical-grade plastic main cylinder having a proximal end and a distal end, at least two angled medical-grade plastic proximal end attachments, said medical-grade plastic proximal end attachments having forty-five, and ninety degree-angles, each angled medical grade plastic proximal end having a fitted opening, said fitted opening configured to be sealably held against an area immediately surrounding a penis, said angled medical-grade plastic proximal end attachments being attachable to the proximal end of the said medical-grade plastic main cylinder, at least one medical-grade plastic weighted distal end attachment, said medical-grade plastic weighted distal end attachment being attachable to the medical-grade plastic main cylinder opposite to the proximal end; and at least one vacuum line attachment and quick release valve connected to the main cylinder, the method comprising the steps of:
   a. a user selecting an angled proximal end attachment for use;
   b. a user attaching the said angled proximal end attachment to the main cylinder;
   c. a user selecting a weighted distal end attachment;
   d. a user attaching the said weighted distal end attachment to the main cylinder;
   e. a user preparing the immediately surrounding a penis for attaching the erectile dysfunction treatment kit;
   f. a user placing a penis through the fitted opening of the attached proximal end into the main cylinder;
   g. a user creating a partial vacuum inside the assembled angled proximal end and main cylinder;
   h. a user applying distractive force on the area surrounding a penis for a recommended therapeutic amount of time: and
   i. a user releasing the said partial vacuum from inside the assembled angled proximal end and main cylinder.

11. The method of claim 10 further comprising the step of inserting a custom fitted sleeve having an outer diameter, an inner diameter, and a sealing interface capable of creating an airtight seal against the area surrounding a penis into the fitted opening of the selected angled medical-grade plastic proximal end attachment with the said outer diameter of the custom fitted sleeve configured to be seated around the fitted opening.

12. The method of claim 10 further comprising the step of changing the angled proximal end attachment to the main cylinder and repeating the method steps of claim 9 as directed.

13. The method of claim 10 further comprising the step of creating different weighted attachments by attaching additional weighted distal end attachments to the erectile dysfunction treatment system.

14. A method of treating erectile dysfunction and related problems using an erectile dysfunction treatment kit having medical-grade plastic main cylinder having a proximal end and a distal end, at least two angled medical-grade plastic proximal end attachments, said medical-grade plastic proximal end attachments having forty-five and ninety degree angles, each angled medical grade plastic proximal end having a fitted opening, said fitted opening configured to be sealably held against an area immediately surrounding a penis, said angled medical-grade plastic proximal end attachments being attachable to the proximal end of the said medical grade plastic main cylinder, at least one medical-grade plastic weighted distal end attachment, said medical-grade plastic weighted distal end attachment being attachable to the medical-grade plastic main cylinder opposite to the proximal end; and at least one vacuum line attachment and quick release valve connected to the main cylinder, the method comprising the steps of:

a. a user creating an erectile dysfunction treatment system by selecting an angled proximal end for use, attaching the said angled proximal end to the main cylinder, selecting a weighted distal end and attaching the said weighted distal end to the main cylinder;

b. a user preparing the area for attaching the erectile dysfunction treatment system;

c. a user placing a penis through the fitted opening of the attached proximal end into the main cylinder;

d. a user creating a partial vacuum inside the attached proximal end; and e. a user manipulating the attached erectile dysfunction treatment system by grasping the said attached erectile dysfunction treatment system by i. holding the attached erectile dysfunction treatment system at different angles for a recommended amount of time and ii. applying a distractive force to the attached erectile dysfunction treatment system by pulling the said attached erectile dysfunction treatment system in a direction away from the area; and f. a user releasing the said partial vacuum from inside the assembled angled proximal end and main cylinder.

15. The method of claim 14 further comprising the step of inserting a custom fitted sleeve having an outer diameter, an inner diameter, and a sealing interface capable of creating an airtight seal against the area surrounding a penis into the fitted opening of the selected angled medical-grade plastic proximal end attachment with the said outer diameter of the custom fitted sleeve configured to be seated around the fitted opening.

16. The method of claim 14 further comprising the step of changing the angled proximal end attachment to the main cylinder and repeating the method steps of claim 13 as directed.

17. The method of claim 14 further comprising the step of creating different weighted attachments by attaching additional weighted distal end attachments to the erectile dysfunction treatment system.

* * * * *